US006326501B1

(12) United States Patent
Jiang

(10) Patent No.: US 6,326,501 B1
(45) Date of Patent: Dec. 4, 2001

(54) METHYLATION OF INDOLE COMPOUNDS USING DIMETHYL CARBONATE

(75) Inventor: Xinglong Jiang, Plainsboro, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/826,977

(22) Filed: Apr. 5, 2001

Related U.S. Application Data

(60) Provisional application No. 60/198,203, filed on Apr. 19, 2000.

(51) Int. Cl.[7] ............... C07D 209/04; C07D 209/10; C07D 209/42
(52) U.S. Cl. ............... 548/469; 548/502; 548/483; 548/494; 548/492
(58) Field of Search ................... 548/492, 494, 548/502, 469, 483

(56) References Cited

U.S. PATENT DOCUMENTS 5,057,614 * 10/1991 Davis et al. ............... 548/466
6,048,887 * 4/2000 Dhingra et al. ............... 514/414

FOREIGN PATENT DOCUMENTS

0746544 B1 * 9/1998 (EP) .

OTHER PUBLICATIONS

Pietro Tundo, Maurizio Selva and Anderea Bomben, Organic Syntheses, vol. 76, 1999 pp. 169–176.*

* cited by examiner

Primary Examiner—Floyd D. Higel
Assistant Examiner—Kamal Saeed
(74) Attorney, Agent, or Firm—George W. Johnston; John P. Parise

(57) ABSTRACT

A process for manufacturing a methylated indole compounds of the formula:

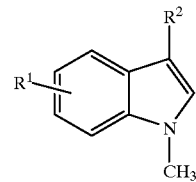

where $R^1$ is selected from the group consisting of halogen, $C_1$–$C_6$ alkyl, $C_1$–$C_6$ alkenyl, —$OCH_3$, —$NO_2$, —CHO, —$CO_2CH_3$, and —CN, and $R^2$ is selected from the group consisting of $C_1$–$C_6$ alkyl, —$CO_2CH_3$, —CN, —CHO, —$NH_2$, —$N(C_1$–$C_6$ alkyl$)_2$, —$(CH_2)_n$COOH, and —$(CH_2)_n$CN, where n is an integer from 1 to 4, inclusive, involves reacting a compound of the formula:

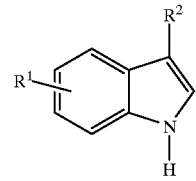

with dimethyl carbonate in the presence of a base or a catalyst at ambient pressure.

21 Claims, No Drawings

METHYLATION OF INDOLE COMPOUNDS USING DIMETHYL CARBONATE

This application claims benefit of Ser. No. 60/198,203 filed on Apr. 19, 2000.

BACKGROUND OF THE INVENTION

1. Field

The invention relates to the use of dimethyl carbonate ("DMC") for the N-methylation of indole compounds.

2. Description

The compound 3-(1-methylindol-3-yl)4-(1-methyl-6-nitroindol-3-yl)-1 H-pyrrole-2,5-dione is a selective inhibitor of protein kinase C ("PKC") and is useful as an antimitotic agent for oral treatment of solid tumors as well as treating autoimmune diseases such as rheumatoid arthritis. This compound is described in U.S. Pat. No. 5,057,614, the contents of which are herein incorporated by reference. A synthetic route for preparing this compound uses methyl iodide as a methylating agent (see for example, U.S. application Ser. No. 09/268,887, the contents of which are herein incorporated by reference, which shows the use of methyl iodide for the N-methylation of an indole to synthesize similar compounds). Unfortunately, methyl iodide is highly toxic and has a low boiling point. The release of methyl iodide into the air is highly restricted. Accordingly, there exists a need for environmentally friendly methods for methylating indole compounds.

The following scheme shows a method for preparing 3-(1-methyl-3-indolyl)4-(1-methyl-6-nitro-3-indolyi)-1 H-pyrrole-2,5-dione.

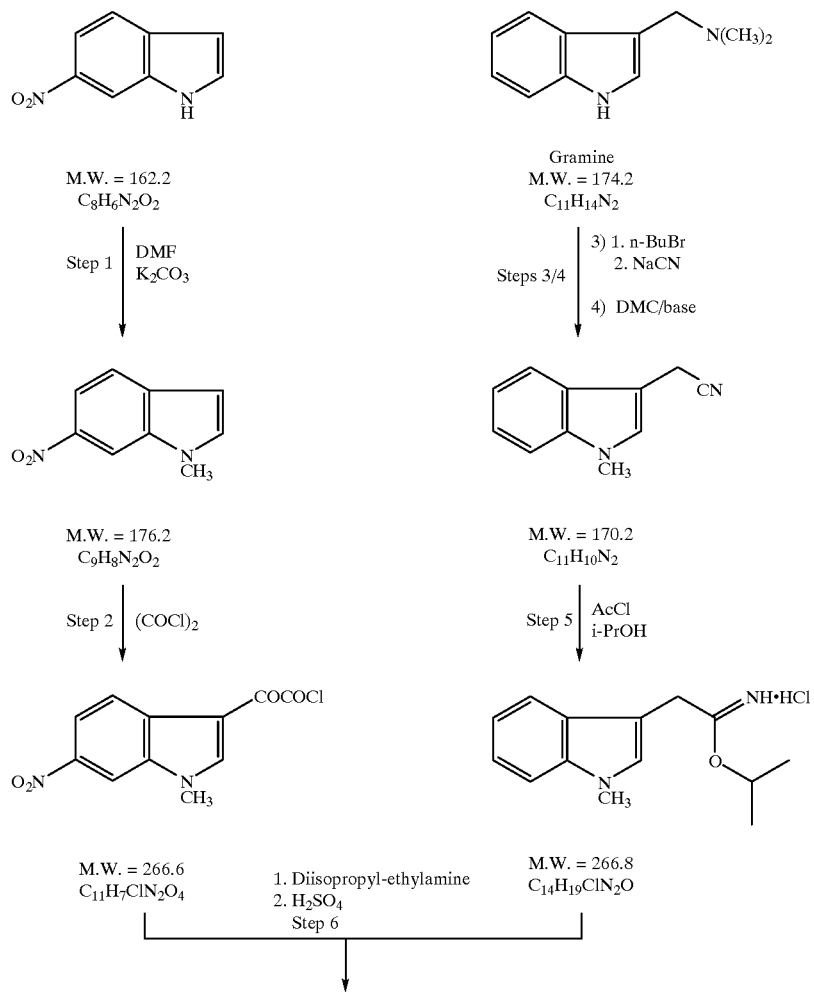

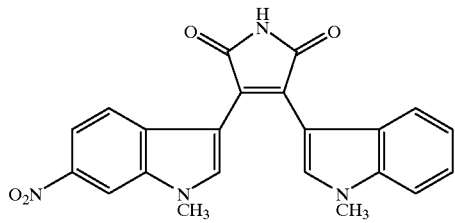

M.W. = 400.4
C$_{22}$H$_{16}$N$_4$O$_4$

Common methylating agents, such as methyl halides (MeX; X=Cl, Br, I) and dimethylsulfate ("DMS", can be used to methylate O—, C— and N— under mild reaction conditions. However, as described above for methyl iodide, these agents pose severe concerns from environmental and process safety standpoints. On the other hand, dimethyl carbonate is a comparatively safe, non toxic and environmentally friendly methylating agent. The by-products of its use, methanol and carbon dioxide, are not associated with disposal problems. Moreover, for the manufacture of antimitotic agents of the above class, which require two indole ring methylations, the need is double. Although it has been reported (Tondo, P., Selva, M., and Bomben, A., Org, Synth. 1998, 76, 169) that DMC can be used to methylate the alpha position of an arylacetonitrile, nowhere has it been suggested to use DMC for methylating indole ring containing compounds, much less the N-methylation of indole rings.

Unfortunately, the use of DMC in prior art processes typically requires high reaction temperatures (>180° C.), a stainless steel autoclave, high pressure, and a large excess of dimethyl carbonate (as solvent and methylating agent). With the help of catalysts, lower reaction temperatures (100° C.) can be used. However, such catalysts (e.g. crown ether) are generally very toxic and pressurized reaction chambers are required.

The inventive use of dimethyl carbonate for N-methylation of an indole ring forms a part of the subject invention and was disclosed in U.S. Provisional Patent Application No. 60/171,557, filed Dec. 22, 1999, which is not publicly available. Although disclosed in this provisional application, the subject invention was not invented by the inventors named in the mentioned provisional patent application and forms no part of the invention claimed in that application.

Therefore, the subject invention fulfills a need in the art for a green process for methylating the nitrogen atom in an indole compound under conditions that do not require high pressure or temperature.

SUMMARY OF THE INVENTION

The subject invention provides a process for manufacturing a methylated indole compounds of the formula:

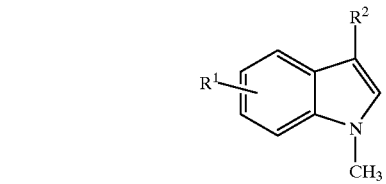

where $R^1$ is selected from the group consisting of halogen, C1–C6 alkyl, $C_1$–$C_6$ alkenyl, —OCH$_3$, —NO$_2$, —CHO, —CO$_2$CH$_3$, and —CN, and $R^2$ is selected from the group consisting of $C_1$–$C_6$ alkyl, —CO$_2$CH$_3$, —CN, —CHO, —NH$_2$, —N($C_1$–$C_6$ alkyl)$_2$, —(CH$_2$)$_n$COOH, and —(CH$_2$)$_n$CN, where n is an integer from 1 to 4, inclusive. The process comprises reacting a compound of the formula:

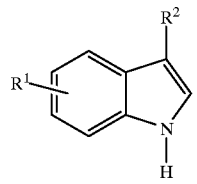

wherein $R^1$ and $R^2$ are as above, with dimethyl carbonate in the presence of a suitable base or catalyst at ambient pressure.

Typically, the reacting is at a temperature between about 120° C. and about 134° C., more preferably between about 126° C. and about 130° C.

It is preferred that the reacting is in the presence of a solvent, such as N,N-dimethylformamide and 1-methyl-2-pyrrolidinone, the most preferred solvent being N,N-dimethylformamide.

Favorably, the reacting is in the presence of a phase transfer catalyst, such as tetrabutylammonium bromide or 18-crown-6, the most favorable catalyst being tetrabutylammonium bromide.

The process can involve reacting is in the presence of a base, such as potassium hydroxide, sodium hydroxide, and potassium carbonate, the most favorable base being potassium carbonate.

Of course the reacting can in the presence of both a base and a catalyst. For example, it is favored where the base is selected from the group consisting of potassium hydroxide, sodium hydroxide, and potassium carbonate, and the catalyst is a phase transfer catalyst. Favored bases are selected from the group consisting of potassium hydroxide, sodium hydroxide, and potassium carbonate, and favored catalysts are selected from the group consisting of tetrabutylammonium bromide and 18-crown-6.

The reaction time can vary but is readily determined by the skilled artisan. Favorable reations times are between 0.75 hour and 36 hours, preferrably between 1 hour and 26 hours, and most preferrably between 1 hour and 10 hours.

Favored compounds include those where $R^1$ is at position 6 and $R^2$ is hydrogen ($R^1$ is favorably nitro) and those where $R^1$ is hydrogen and $R^2$ is acetonitrile.

DETAILED DESCRIPTION OF THE PREFERRED EMBODIMENTS

The invention will now be described in terms of its preferred embodiments. These embodiments are set forth to aid in understanding the invention but are not to be construed as limiting.

The subject N-methylation process typically requires only 2.2 equivalents of dimethyl carbonate, reasonable temperature, and ambient pressure. The term "ambient pressure" is used herein to reflect normal atmospheric pressure. The exemplified processes below generally needs only catalytic amounts of tetrabutylammonium bromide ("TBAB") or 18-crown-6 without the use of a base. Alternatively, or additionally, a base such as potassium hydroxide, sodium hydroxide, or potassium carbonate can by utilized. Both potassium carbonate and TBAB are easily eliminated from the product by the following an isolation procedure that involves the addition of water. Catalytic amounts of TBAB or 18-crown-6, as well as appropriate amounts of base, for example potassium hydroxide, sodium hydroxide or potassium carbonate, are readily determinable by the skilled artisan. Generally, these amounts will be for TBAB in the range of about five percent (5%) by weight to about eighty percent (80%) by weight of catalyst to substrate. A preferred range is from about twenty percent (20%) by weight to about forty percent (40%) by weight of catalyst to substrate, with the range of from about twenty percent (20%) by weight to about thirty percent (30%) by weight of catalyst to substrate being most preferred. For 18-crown-6, the amounts will generally be in the range of about five percent (5%) by weight to about ten percent (10%) by weight of catalyst to substrate. Preferably, the 18-crown-6 is present at about five percent (5%) by weight of catalyst to substrate.

The subject process can proceed by mixing an indole substrate with dimethyl carbonate in the presence of a base or a catalyst in a suitable solvent, such as N,N-dimethylformamide ("DMF") or 1-methyl-2-pyrrolidinone ("NMP"), followed by heating the reaction mixture to reflux for a short time (normally 2 to 3 hours). The choice of reaction temperature is readily determinable by the skilled artisan. The reaction temperature will normally be above the boiling point of the reagent, around 90° C. for DMC. The reaction can be quenched by adding water, after which the product can be obtained either by filtration or by extraction with a suitable solvent. The subject process typically results in the desired product in good yield with high quality. For example, when 6-nitroindole was used to conduct the reaction, 96% of 1-methyl-6-nitroindole was obtained in 99.5% (by weight) purity. Only 0.3% of one impurity was detected.

The process described below is a general procedure. If the product is not solid, filtration is not necessary, instead, the desired product can be extracted from the aqueous mixture by using a suitable solvent, for example, tert-butyl methyl ether, or ethyl acetate.

The effect of various substituents on the methylation of an indole system using DMC was investigated. Table 1 records the effects of several electron-withdrawing functional groups on the N-methylation reaction. There was not much difference found in terms of either reason time or the yields obtained of N-methylated indoles when the functional groups are present on the phenyl ring or the pyrrole ring of the indole system. All substrates tested with this method afforded high yields (>95%), except in the case of indole-3-carboxaldehyde where the corresponding N-methylated indole was obtained in 85% yield.

TABLE 1

Effect of Electron Withdrawing Substituents of the N-Methylation of Indoles

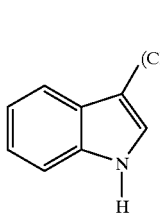

| R | reaction time (h) | Desired product yield (%) |
|---|---|---|
| 3-CN | 3.5 | 97 |
| 4-NO$_2$ | 2 | 96 |
| 5-NO$_2$ | 3 | 97 |
| 6-NO$_2$ | 2 | 97 |
| 5-Br | 3.5 | 95 |
| 6-Cl | 3.5 | 96 |
| 3-CHO | 3.5 | 85 |
| 3-CO$_2$CH$_3$ | 3.5 | 96 |

The R group can be at any position of the indole system except position 1. The reaction between indole-3-carboxylic acids and dimethyl carbonate was also investigated. The selectivity between O-methylation and N-methylation was not as high as would be expected. However, as expected, under the reaction conditions, esterfication of a carboxyl group was somewhat faster than N-methylation. For example, the reaction of indole-3-propionic acid with dimethyl carbonate in the presence of potassium carbonate in OMF afforded both an O,N-dimethylated substance in 65% yield after 4 hours at refluxing temperature, together with 30% of the O-methylated product. After the reaction mixture was heated to reflux for another 4 hours, only O,N-dimethylated product was obtained in 93% isolated yield. As demonstrated in Table 2, similar results were observed with indole-3-acetic acid. But when indole-3-carboxylic acid was subjected to the typical reaction conditions, along with 50% of the dimethylated product obtained, 45% of N-methylindole was isolated, formed as a result of decarboxylation of indole-3-carboxylic acid at the reaction temperature (128° C.).

TABLE 2

Differences in the Rates of N- and O-Methylation of Indolecarboxylic Acids with Dimethyl Carbonate.

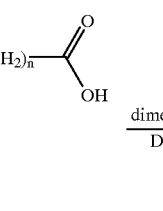

TABLE 2-continued (structure shown: indole with (CH₂)ₙ-C(=O)-OR substituent at 3-position, R¹ on N)

| n | Reaction time (h) | Product yield (%) |
|---|---|---|
| 0 | 5 | R = R₁ = Me (50) |
|   |   | N-Methylindole (45) |
| 1 | 6 | R = R₁ = Me (89) |
|   |   | R = Me, R₁ = H (8) |
|   | 8 | R = R₁ = Me: 95 |
| 2 | 4 | R = R₁ = Me (65) |
|   |   | R = Me, R₁ = H (30) |
|   | 8 | R = R₁ = Me (93) |

As above, the substituent could be attached at any position of the indole nucleus except at position 1.

With dimethyl carbonate as a methylating agent, the N-methylation of indole system containing electron-donating groups was also studied. For an example, N-methylation of 5-methoxyindole with dimethyl carbonate at reflux temperature for 5 hours gave 1-methyl-5-methoxyindole in 97% isolated yield. However, other indole substrates, such as gramine, indole-3-methanol, indole3-ethanol and tryptamine gave a complex mixture of unidentified products. These results indicated that N-methylation with dimethyl carbonate is not applicable to such indole systems.

To further illustrate the utility of this method, indole-3-acetonitrile was used as a substrate to examine the selectivity between methylation of an indole nitrogen and C-methylation of an activated methylene group present in the molecule. As can be seen in Table 3 however, dimethyl carbonate can be used to preferentially N-methylate indole-3-acetonitriles with only a small amount of concurrent C-methylation by varying the reaction conditions. In the presence of potassium carbonate, indole-3-acetonitrile gave, along with 89% of the expected product 1-methylindol-3-acetonitrnle, the C,N-dimethylated by-product, rac.-2-(1-methylindol-3-yl)propionitrile in 8% yield. With the assistance of a phase transfer catalyst ("PTC"), such as 18-crown-6 or tetrabutylammonium bromide, the formation of the dimethylated by-product was suppressed to about 3%. Under the latter reaction conditions, about 90% of the desired product, 1-methylindole-3-acetonitrile was isolated.

Scheme 3

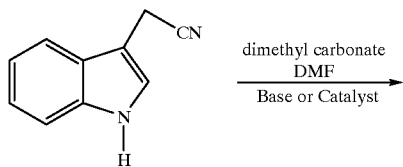

dimethyl carbonate
DMF
Base or Catalyst

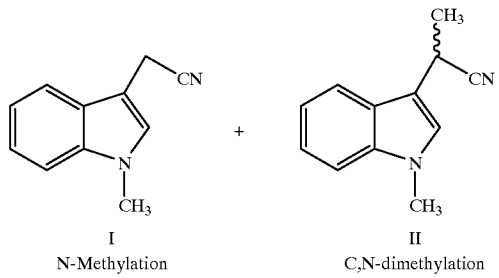

I
N-Methylation

II
C,N-dimethylation

TABLE 3

Selectivity between N- and C-methylation of Indole-3-Acetonitrile

| base | catalyst | Composition of crude reaction product (anal. HPLC) | | Isolated yield |
|---|---|---|---|---|
| | | I | II | I + II |
| K₂CO₃ | | 89% | 8% | 89% |
| K₂CO₃ | n-Bu₄NBr | 86.6% | 9.7% | 90.5% |
| | n-Bu₄NBr | 93.8% | 2.9% | 91.5% |
| KOH | n-Bu₄NBr | 94.4% | 3.1% | 80% |
| NaOH | 18-crown-6 | 91% | 3% | 78% |

EXAMPLES

The experiments in the following examples have actually been performed.

Example 1

Preparation of 1-methylindole-3-acetonitrile

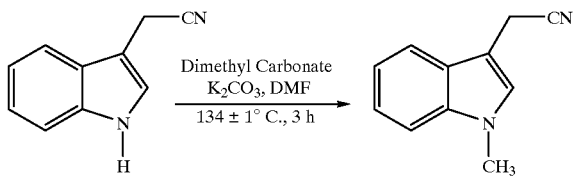

Dimethyl Carbonate
K₂CO₃, DMF
134 ± 1° C., 3 h

A 500 mL, three-necked flask equipped with a thermocouple, condenser, and addition funnel was charged with indole-3-acetonitrile (10.0 g, 0.064 mol), potassium carbonate (5.0 g, 36 mmol), N,N-dimethylformamide (60 mL) and dimethyl carbonate (11.0 mL, 0.13 mol). The resulting mixture was heated to 124±1° C. The progress of the reaction was monitored by HPLC. After 10 h at this temperature, the presence of the starting indole could not be detected. The reaction mixture was then cooled to zero to −5° C. Water (140 mL) was added which resulted in the formation of a precipitate. The mixture was stirred at −5° C. for 1 hour, then the solid was collected by filtration, washed with water (150 mL), and dried under high vacuum at 45° C. for 24 h to give 1-methylindole-3-acetonitrile (I and II, 9.69 g, 89%) as a brown solid.

Example 2

Synthesis of 1-methylindole-3-acetonitrile and rac.-2-(1-methylindol-3-yl)propionitrile.

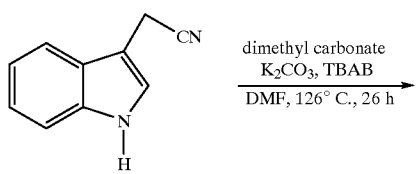

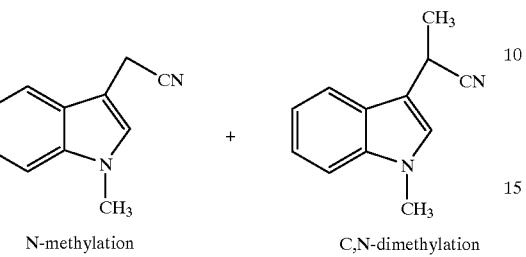

N-methylation (86.6%) + C,N-dimethylation (9.7%)

A mixture of indole-3-acetonitrile (5.0 g, 32.01 mmol), potassium carbonate (powder, 2.5 g), dimethyl carbonate (10 mL, 118.8 mmol), N,N-dimethylformamide (40 mL) and tetrabutylammonium bromide 0.5 g were mixed together and heated to 126° C. for 6 h. Then a second portion of dimethyl carbonate (3 mL, 35.6 mmol) was added and mixture was refluxed for another 17 h. Starting material was still present, so an third portion of dimethyl carbonate (3 mL, 35.6 mmol ) was added and the reaction mixture was refluxed for another 3 h. Analysis of the reaction mixture at this point showed it to be mainly a mixture of two compounds, 1-methylindole-3-acetonitrile (86.6%) along with a second minor component identified as rac.-2-(1-methylindol-3-yl)propionitrile (9.7%). Starting indole could not be detected. The reaction mixture was cooled to room temperature, then was diluted with water (80 mL) and extracted with tert-butyl methyl ether (100 mL) The separated organic layer was washed twice with water (100 mL) then the solution was concentrated under vacuum to ~20 mL. The concentrate was cooled in an ice-bath as heptane (100 mL) was added drop-wise with vigorous stirring. The mixture was cooled to −15° C. and the resulting solid was filtered off, washed with heptane (50 mL) and dried under vacuum at 25° C. to give 1-methylindole-3-acetonitrile (1) and rac.-2-(1-methylindol-3-yl)propionitrile (II).

Example 3

Preparation of 1-methylindole-3-acetonitrile.

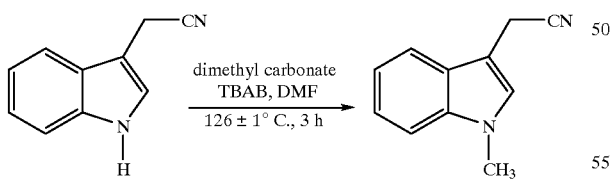

A 1 L, three-necked flask equipped with a thermocouple, condenser, and addition funnel was charged with indole-3-acetonitrile (58.0 g, 90% pure=0.334 mol), tetrabutylammonium bromide (11.6 g, 36 mmol), N,N-dimethylformamide (348 mL) and dimethyl carbonate (92.8 mL, 1.10 mol) and the resulting mixture was heated to 126±1° C. The progress of the reaction was monitored by HPLC and after 3 h at this temperature, the presence of remaining starting indole could not be detected. After the reaction mixture was then cooled to zero to −5° C., water (696 mL) was added which resulted in the formation of a precipitate. The mixture was stirred at −5° C. for 1 hour, then the solid was collected by filtration, washed with water (150 mL) and dried under high vacuum at 45° C. for 24 h to give 1-methylindole-3-acetonitrile (52.0 g, 91.5%) as a brown solid.

Example 4

Synthesis of 1-methylindole-3-acetonitrile and rac.-2-(1-methylindol-3-yl)propionitrile.

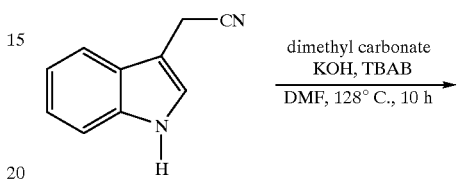

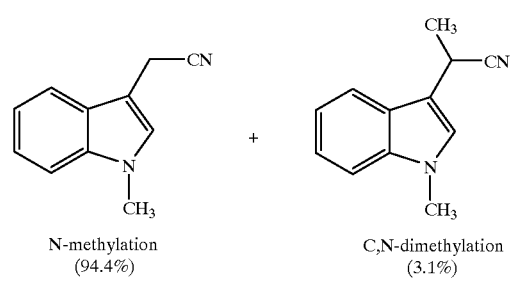

N-methylation (94.4%) + C,N-dimethylation (3.1%)

A mixture of indole-3-acetonitrile (4.0 g, 25.6 mmol), potassium hydroxide (pallet, 2.5 g), dimethyl carbonate (8 mL, 94.9 mmol), N,N-dimethylformamide (50 mL) and tetrabutylammonium bromide 0.5 g were mixed together and heated to 128° C. for 10 h. Analysis of the reaction mixture at this point showed it to be mainly a mixture of two compounds, 1-methylindole-3-acetonitrile (94.4%) along with a second minor component identified as rac.-2-(1-methylindol-3-yl)propionitrile (3.1%). Starting indole could not be detected. The reaction mixture was cooled to room temperature, then was diluted with water (120 mL). The mixture was cooled to −15° C., and the precipitate was formed. The mixture was stirred at this temperature for 1 h. The resulting solid was filtered off, washed with heptane (50 mL) and dried under vacuum at 25° C. to give 3.60 g of 1-methylindole-3-acetonitrile(I) and C,N-dimethylated by-product (II).

Example 5

Synthesis of 1-methylindole-3-acetonitrile and rac.-2-(1-methylindol-3-yl)propionitrile.

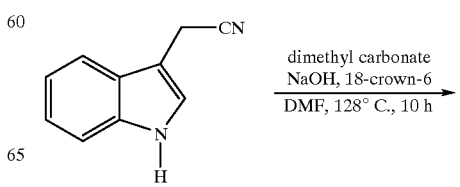

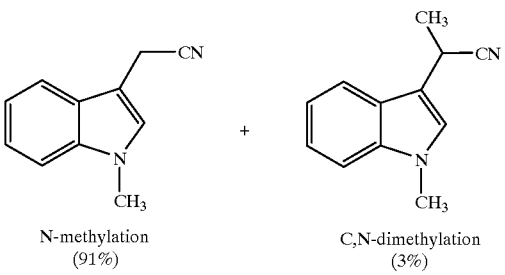

N-methylation (91%) + C,N-dimethylation (3%)

A 250 mL, three-necked flask was charged with indole-3-acetonitrile (5.0 g, 32.0 mmol), sodium hydroxide (pallet, 2.5 g), dimethyl carbonate (6.6. mL, 78.3 mmol), N,N-dimethylformamide (40 mL), and 25 mg of 18-crown-6. The resulting mixture was heated to 127 ° C. for 10 h. Analysis of the reaction mixture at this point showed it to be mainly a mixture of two compounds, 1-methylindole-3-acetonitrile (90.8%) along with a second minor component identified as rac.-2-(1-methylindol-3-yl)propionitrile (3.0%). No starting indole was detected. The reaction mixture was cooled to room temperature, then was diluted with water (100 mL). The mixture was cooled to −15° C., and a precipitate formed. The mixture was stirred at this temperature for 1 h. The resulting solid was filtered off, washed with heptane (50 mL), and dried under vacuum at 25° C. to give 4.3 g of 1-methylindole-3-acetonitrile(1) and C,N-dimethylated by-product (II).

Example 6

Preparation of 1-methylindole-3-carbonitrile.

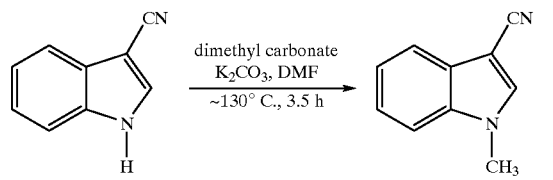

A mixture of indole-3-carbonitrile (1.0 g, 7.03 mmole), potassium carbonate (0.5 g), N,N-dimethytformamide (10 mL) and dimethyl carbonate (1.8 mL, 21.4 mmol) was stirred and heated to reflux (~130° C.). The reaction (monitored by HPLC) was complete within 3.5 h. The reaction mixture was then cooled to 3° C. and ice cold water (25 mL) was added slowly. The resulting oily suspension was extracted with tert-butyl methyl ether (40 mL) and the organic phase was washed with water (3×25 mL), dried and evaporated in vacuo to obtain 1.07 g of the product, 1-methylindole-3-carbonitrile, as a dark oil (97.4% yield).

Example 7

Preparation of 5-bromo-1-methylindole.

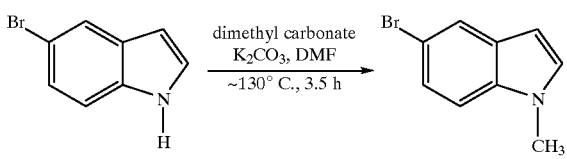

5-Bromoindole (3.0 g, 15.38 mmol), potassium carbonate (1.5 g), N,N-dimethylformamide (20 mL) and dimethyl carbonate (3.9 mL, 46 mmol) were stirred and heated to reflux (~130° C.) for 3.5 h. The reaction was monitored by HPLC. The mixture was then cooled to ~3° C., and the slow addition of ice cold water (50 mL) resulted in the separation of the product as a light brown oil. The mixture was extracted with tert-butyl methyl ether (40 mL) and the organic layer was washed with water (3×25 mL). The solvent was evaporated under reduced pressure to furnish 3.06 g of 5-bromo-1-methylindole as a light brown oil (94.8% yield).

Example 8

Preparation of 6-chloro-1-methylindole.

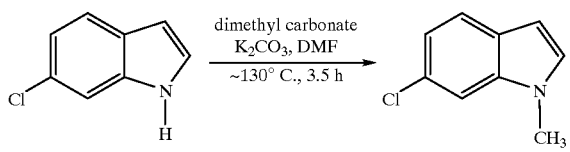

6-Chloroindole (1.0 g, 6.59 mmol), potassium carbonate (0.5 g), N,N-dimethylformamide (10 mL) and dimethyl carbonate (1.7 mL, 20.21 mmol) were stirred and heated to reflux (~130° C.). The starting indole was consumed within 3.5 h (as determined by HPLC). After the mixture was then cooled to ~3° C., ice cold water (50 mL) was added and the resulting oily suspension was extracted with tert-butyl methyl ether (40 mL). The separated organic layer was washed with water (3×25 mL), then was evaporated under vacuum to furnish 5-chloro-1-methylindole as a light yellow oil (1.05 g, 96.1% yield).

Example 9

Preparation of 1-methylindole-3-carboxaldehyde.

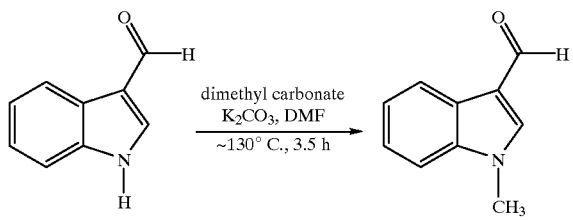

A mixture of indole-3-carboxaldehyde (3 g, 20.67 mmol), potassium carbonate (1.5 g), N,N-dimethylformamide (20 mL) and dimethyl carbonate (5.2 mL, 61 mmol) were stirred and heated to reflux (~130° C.). At various time intervals, the progress of the reaction was monitored by HPLC and it was shown to be complete within 3.5 h. The reaction mixture was cooled down to ~3° C. and ice cold water (60 mL) was slowly added. The resulting dark oily suspension was extracted with tert-butyl methyl ether (60 mL) and the organic layer was washed with water (2×50 mL). The organic extract was evaporated under reduced pressure to provide 1-methylindole-3-carboxalehyde as a dark brown oil (1.98 g, 85% yield).

Example 10

Preparation of 1-methylindole-3-carboxylic acid methyl ester.

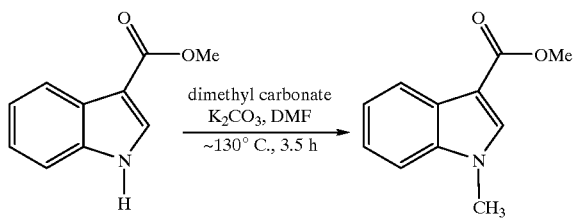

Indole-3-carboxylic acid methyl ester (5.0 g, 28.54 mmol), potassium carbonate (2.5 g), N,N-dimethylformamide (35 mL) and dimethyl carbonate (7.2 mL, 85 mmol) were combined and the stirred mixture was heated to reflux (~130° C.). Within 3.5 h, the reaction had gone to completion as determined by HPLC analysis. After the reaction mixture was cooled to ~3° C., ice cold water (100 mL) was slowly added. The resulting slightly off-white solid was recovered by filtration and was washed with water (2×50 mL). The solid was not purified further, but was dried in vacuo at 45° C. for 24 h to provide 5.2 g of 1-methylindole-3-carboxylic acid methyl ester (96.3% yield).

Example 11

Preparation of 5-methoxy-1-methylindole.

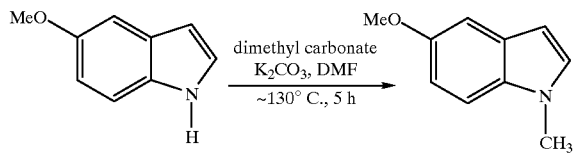

A mixture of 5-methoxyindole (1 g, 6.79 mmol), potassium carbonate (0.5 g), N,N-dimethylformamide (10 mL) and dimethyl carbonate (1.7 mL, 20 mmol) was stirred and heated to reflux (~130° C.). The progress of the reaction was monitored by HPLC. Within 5 h, the starting indole had been consumed and after the mixture was cooled to ~3° C., it was treated with ice cold water (30 mL). The formed precipitate was filtered off, then was washed in turn with water (2×30 mL) and hexanes (30 mL). The colorless product was dried under vacuum at 25° C. for 48 h to afford 5-methoxy-1-methylindole (1.067 g, 97.4% yield).

Example 12

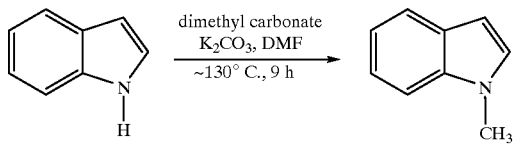

Preparation of 1-methylindole.

Indole (10 g, 85.4 mmole), potassium carbonate (5 g), N,N-dimethylformamide (70 mL) and dimethyl carbonate (11 mL, 0.13 mol) were mixed together and refluxed (~130° C.) for 2 h. At this point TLC analysis of the reaction showed two compounds, the N-methylated indole along with a significant amount of starting material. The reaction mixture was cooled down to ~50° C. and a second portion of dimethyl carbonate (5.5 mL, 0.065 mol) was added. The mixture was heated at reflux for another 7 h until TLC analysis indicated total consumption of starting indole. The reaction mixture was cooled down to room temperature and it was slowly diluted with water (150 mL). The resulting mixture was extracted with tert-butyl methyl ether (150 mL) and the separated organic layer was washed with water (2×100 mL). The solvent was evaporated in vacuao to furnish 10.8 g of 1-methylindole as light yellow oil (96.5% yield).

Example 13

Preparation of 1-methylindoline.

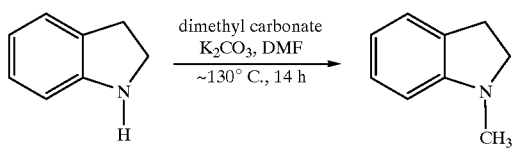

Indoline (3 g, 0.025 mol), potassium carbonate (1.59), N,N-dimethylformamide (20 mL) and dimethyl carbonate (6.4 mL ,0.076 mol) were mixed together and heated to reflux (around 130 ° C.) for 14 h. The reaction, monitored by HPLC, went to completion within 14 h. The reaction mixture was cooled down to room temperature, then was slowly diluted with water (50 mL) and extracted with tert-butyl methyl ether (60 mL ). The organic extract was washed with water (3×50 mL) and the solution was evaporated to constant weight under reduced pressure to furnish 3.13 g of the product, N-methylindoline as a light yellow oil (95% yield).

Example 14

Synthesis of 1-methyl-5-nitroindole.

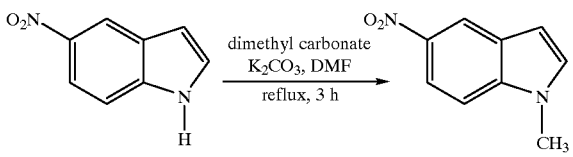

A 500 mL, three-necked flask equipped with a thermocouple, condenser, and addition funnel was charged with 5-nitroindole (20.0 g, 12.3 mmol), potassium carbonate (4.0 g, 29 mmol), N,N-dimethylformamide (80 mL) and dimethyl carbonate (22 mL, 26.14 mmol). The resulting mixture was heated to reflux. The reaction was monitored by HPLC or TLC (solvent system: 30% ethyl acetate in heptane). An analysis of the reaction mixture after 3 h at reflux, by the above methods, failed to detect any remaining 5-nitroindole. The reaction mixture was then cooled to 10±5° C. and diluted with water (160 mL) which resulted in the formation of a yellow precipitate. After the mixture was stirred at room temperature for 2 h, the solid was collected by filtration, then was washed with water (100 mL) and dried under high vacuum at 60–65° C. for 24 h to give 1-methyl-4-nitroindole (21.1 g, 97.1%) as a yellow solid.

Example 15

Synthesis of 1-methyl-4-nitroindole.

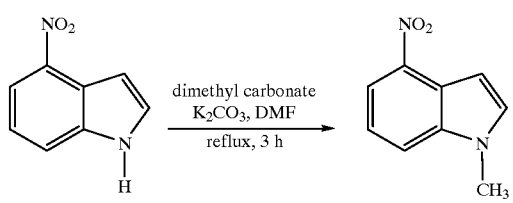

1-methyl-4-nitroindole was prepared from 4-nitroindole in 96% yield using the same experimental conditions and isolation procedure described in Example 11 for the preparation of the isomeric 1-methyl-4-nitroindole.

Example 16

Preparation of 1-methylindole-3-carboxylic acid methyl ester and 1-methylindole.

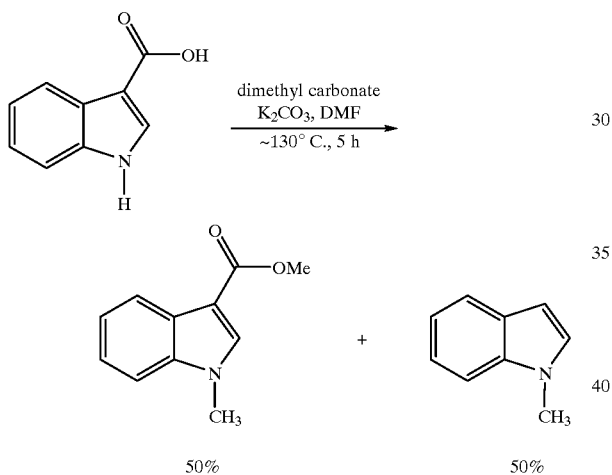

To a three-necked round bottom flask was charged 3-indolecarboxylic acid (2.5 g, 15.51 mmol), potassium carbonate (powder, 1.25 g), N,N-dimethylformamide (20 mL) and dimethyl carbonate (3.9 mL, 46.3 mmol). As the stirred mixture was heated to reflux (130° C.), the disappearance of starting indole was monitored by HPLC. After 5 h the reaction was complete, then the mixture was cooled to room temperature and was partitioned between water (50 mL) and tert-butyl methyl ether (100 mL). The separated organic layer was washed with water (2×50 mL) and the volatiles were evaporated under reduced pressure. Purification of the obtained crude by using column chromatography over silica gel furnished 1-methylindole-3-carboxylic acid methyl ester (50% yield) and the decarboxylated byproduct 1-methylindole (45% yield).

Example 17

Preparation of 1-methylindole-3acetic acid methyl ester and 1-indole-3-acetic acid methyl ester.

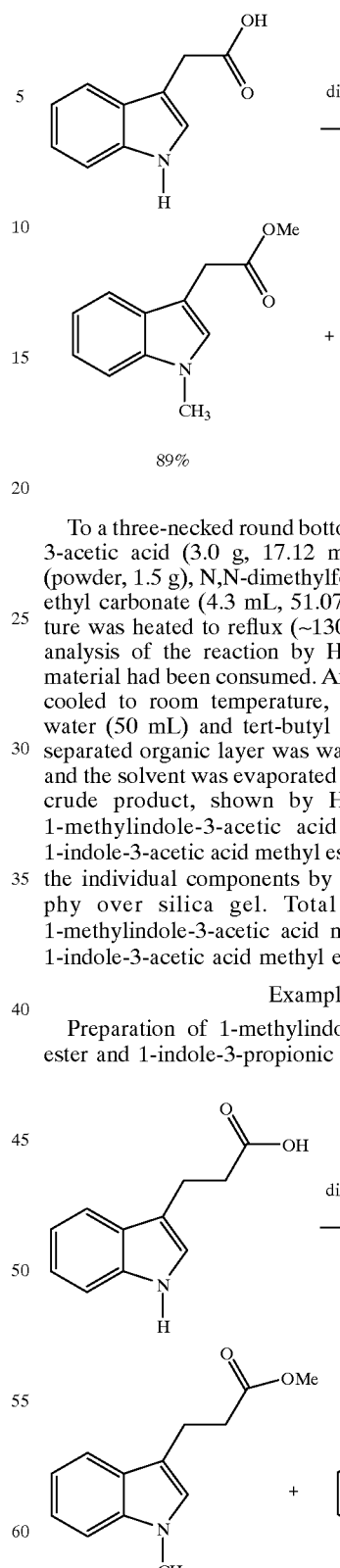

To a three-necked round bottom flask was charged indole-3-acetic acid (3.0 g, 17.12 mmol), potassium carbonate (powder, 1.5 g), N,N-dimethylformamide (20 mL) and dimethyl carbonate (4.3 mL, 51.07 mmol). The resulting mixture was heated to reflux (~130° C.) for 6 h at which time analysis of the reaction by HPLC indicated the starting material had been consumed. After the reaction mixture was cooled to room temperature, it was partitioned between water (50 mL) and tert-butyl methyl ether (60 mL). The separated organic layer was washed with water (2×50 mL) and the solvent was evaporated under reduced pressure. The crude product, shown by HPLC analysis to contain 1-methylindole-3-acetic acid methyl ester (89%) and 1-indole-3-acetic acid methyl ester (8%), was separated into the individual components by using column chromatography over silica gel. Total yield 3.2 g, 2.8 g for 1-methylindole-3-acetic acid methyl ester and 0.40 g for 1-indole-3-acetic acid methyl ester.

Example 18

Preparation of 1-methylindole-3-propionic acid methyl ester and 1-indole-3-propionic acid methyl ester.

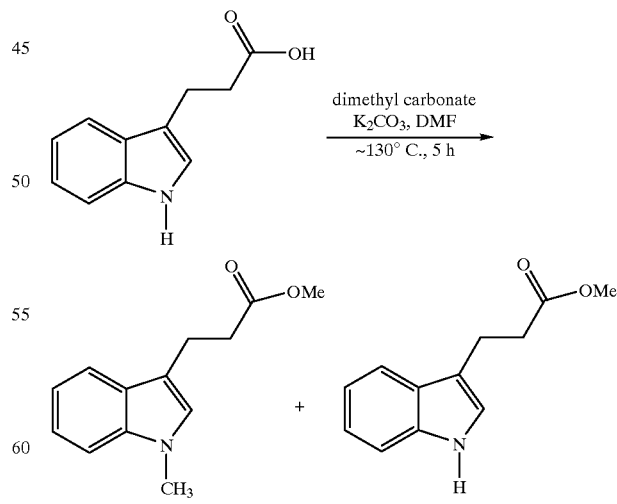

A stirred mixture of indole-3-propionic acid (1.0 g, 5.28 mmol), potassium carbonate (powder, 0.25 g), N,N- dimethylformamide (10 mL) and dimethyl carbonate (1.33 mL, 15.7 mmol) was heated to reflux (~130° C.). After the reaction had been stirred for 5 h at reflux, no detectable levels of starting material remained, as determined by HPLC analysis. The reaction mixture was cooled to room temperature, then was diluted with water (25 mL) and extracted with tert-butyl methyl ether (40 mL). The organic layer was washed with water (2×50 mL) and the solution was concentrated under reduced pressure. The crude product, shown by HPLC analysis to contain 1-methylindole-3-propionic acid methyl ester (65%) and 1-indole-3-propionic acid methyl ester (30%), was separated into the individual products by using column chromatography over silica gel. Total yield 1.01 g, 0.66 g for 1-methylindole-3-propionic acid methyl ester. 0.35 g for 1-indole-3-propionic acid methyl ester.

Example 19

Preparation of 1-methyl-6-nitroindole.

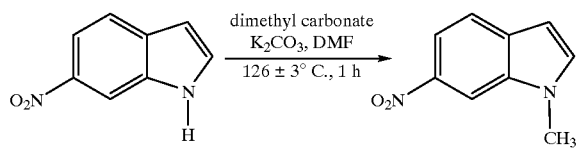

A 1L, three-necked flask equipped with a thermocouple, condenser, and addition funnel was charged with 6-nitroindole (60.0 g, 0.37 mol), potassium carbonate (12.0 g, 87 mmol), N,N-dimethylformamide (240 mL) and dimethyl carbonate (66 mL, 0.784 mol) and the resulting stirred mixture was heated to 126±3° C. The progress of the reaction was monitored by HPLC or TLC (solvent system: 30% ethyl acetate in heptane). After 1 h at this temperature, residual 6-nitroindole could not be detected. Then, the reaction mixture was cooled to 10±5° C. and slowly diluted with water (480 mL). As the water was added, a yellow precipitate formed. The resulting mixture was stirred at room temperature for 2 h, then the solid was recovered by filtration, washed with water (250 mL) and dried under high vacuum at 60–65° C. for 24 h to give 62.6 g of 1-methyl6-nitroindole (96.1% yield) as a yellow solid.

What is claimed is:

1. A process for manufacturing a methylated indole compounds of the formula:

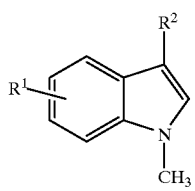

where $R^1$ is selected from the group consisting of halogen, $C_1$–$C_6$ alkyl, $C_1$–$C_6$ alkenyl, —$OCH_3$, —$NO_2$, —CHO, —$CO_2CH_3$, and —CN, and $R^2$ is selected from the group consisting of $C_1$–$C_6$ alkyl, —$CO_2CH_3$, —CN, —CHO, —$NH_2$, —N($C_1$–$C_6$ alkyl)$_2$, —$(CH_2)_n$COOH, and —$(CH_2)_n$CN, where n is an integer from 1 to 4, inclusive, which comprises reacting a compound of the formula:

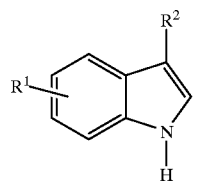

wherein $R^1$ and $R^2$ are as above, with dimethyl carbonate in the presence of a suitable base or catalyst at ambient pressure.

2. The process of claim 1, wherein the reaction occurs is at a temperature between about 120° C. and about 134° C.

3. The process of claim 2, wherein the reaction occurs is at a temperature between about 126° C. and about 130° C.

4. The process of claim 1, wherein the reaction occurs is in the presence of a solvent.

5. The process of claim 4, wherein the reaction occurs is in the presence of a solvent selected from the group consisting of N,N-dimethylformamide and 1-methyl-2-pyrrolidinone.

6. The process of claim 5, wherein the reaction occurs is in the presence N,N-dimethylformamide.

7. The process of claim 1, wherein the reaction occurs is in the presence of a phase transfer catalyst.

8. The process of claim 7, wherein the reaction occurs is in the presence of a phase transfer catalyst selected from the group consisting of tetrabutylammonium bromide or 18-crown-6.

9. The process of claim 8, wherein the phase transfer catalyst is tetrabutylammonium bromide.

10. The process of claim 1, wherein the reaction occurs is in the presence of a base.

11. The process of claim 10, wherein the reaction occurs is in the presence of a base selected from the group consisting of potassium hydroxide, sodium hydroxide, and potassium carbonate.

12. The process of claim 11, wherein the reaction occurs is in the presence of potassium carbonate.

13. The process of claim 1, wherein the reaction occurs is in the presence of both a base and a catalyst.

14. The process of claim 13, wherein the reaction occurs is in the presence of a base selected from the group consisting of potassium hydroxide, sodium hydroxide, and potassium carbonate, and a catalyst which is a phase transfer catalyst.

15. The process of claim 14, wherein the reaction occurs is in the presence of a base selected from the group consisting of potassium hydroxide, sodium hydroxide, and potassium carbonate, and a catalyst selected from the group consisting of tetrabutylammonium bromide and 18-crown-6.

16. The process of claim 1, wherein the reaction occurs is for a time between 0.75 hour and 36 hours.

17. The process of claim 16, wherein the reaction occurs is for a time between 1 hour and 26 hours.

18. The process of claim 17, wherein the reaction occurs is for a time between 1 hour and 10 hours.

19. The process of claim 1, wherein $R^1$ is at position 6 and $R^2$ is hydrogen.

20. The process of claim 19, wherein $R^1$ is nitro.

21. The process of claim 1, wherein $R^1$ is hydrogen and $R^2$ is acetonitrile.

* * * * *